United States Patent
Yabu

(10) Patent No.: US 12,204,233 B2
(45) Date of Patent: Jan. 21, 2025

(54) IMAGING DEVICE

(71) Applicant: SCREEN HOLDINGS CO., LTD., Kyoto (JP)

(72) Inventor: Mitsuhiro Yabu, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 127 days.

(21) Appl. No.: 18/160,434

(22) Filed: Jan. 27, 2023

(65) Prior Publication Data

US 2023/0305369 A1     Sep. 28, 2023

(30) Foreign Application Priority Data

Mar. 24, 2022   (JP) .................................. 2022-048162

(51) Int. Cl.
*G03B 17/48* (2021.01)
*G01N 1/28* (2006.01)
(Continued)

(52) U.S. Cl.
CPC ............... *G03B 17/48* (2013.01); *G01N 1/28* (2013.01); *G01N 33/574* (2013.01); *G12B 9/08* (2013.01); *H04N 23/51* (2023.01); *H04N 23/56* (2023.01)

(58) Field of Classification Search
None
See application file for complete search history.

(56) References Cited

U.S. PATENT DOCUMENTS 9,207,162 B2 * 12/2015 Miyake .................. G06V 20/69
2002/0009391 A1 * 1/2002 Marquiss ............. G01N 35/028
422/65

(Continued)

FOREIGN PATENT DOCUMENTS

JP    2018-040569 A    3/2018
WO      96/21855 A1    7/1996
WO   2020/219495 A1   10/2020

OTHER PUBLICATIONS

Extended European Search Report issued in corresponding European Patent Application No. 23153001.5-1001, dated Aug. 28, 2023.

*Primary Examiner* — Rodney E Fuller
(74) *Attorney, Agent, or Firm* — Rimon P.C.

(57) ABSTRACT

An imaging device acquires images of a plate-like specimen container having a rectangular shape as seen in top view. The imaging device includes a table, a position reference member, and a holding mechanism. The position reference member includes a first extension and a second extension which intersect at right angles to each other. The holding mechanism includes a rotating plate extending horizontally in plate-like form, and a main body portion for pivoting the rotating plate forwardly in a circumferential direction by means of elastic force of a spring. The rotating plate includes a front wing portion, and a protruding portion protruding forwardly in the circumferential direction from the front wing portion. The specimen container is urged in a second direction to align along the first extension when the rotating plate is pivoted to bring the front wing portion into contact with the specimen container. The specimen container is urged in a first direction to align along the second extension when the protruding portion comes in contact with the specimen container. Thus, the specimen container is aligned and placed in a previously determined position in the imaging device.

8 Claims, 10 Drawing Sheets

(51) Int. Cl.
*G01N 33/574* (2006.01)
*G12B 9/08* (2006.01)
*H04N 23/51* (2023.01)
*H04N 23/56* (2023.01)

(56) References Cited

U.S. PATENT DOCUMENTS

2020/0278523 A1* 9/2020 Matsubara ............ H04N 23/695
2022/0244188 A1* 8/2022 Krivoy ............. G01N 35/00732

* cited by examiner

IMAGING DEVICE

RELATED APPLICATIONS

This application claims the benefit of Japanese Application No. 2022-048162, filed on Mar. 24, 2022, the disclosure of which is incorporated by reference herein.

BACKGROUND OF THE INVENTION

Field of the Invention

The present invention relates to an imaging device for acquiring images of a specimen container.

Description of the Background Art

In the fields of medicine, drug discovery, and the like, cells and the like cultured in a specimen container known as a "well plate", a "microplate", and the like have been conventionally observed as specimens. Such a specimen container has a plurality of recessed specimen storage portions known as wells. In general, specimens are put into the wells together with a liquid culture medium. In recent years, such specimens have been imaged by an imaging device equipped with a CCD camera or the like, and observed using image data obtained by the imaging. For example, in cancer drug discovery research, cancer cells have been observed and analyzed by imaging the cancer cells put into the wells together with a liquid (culture solution) as the culture medium by means of an imaging device. Such an imaging device is disclosed, for example, in Japanese Patent Application Laid-Open No. 2018-040569.

The imaging device (1) disclosed in Japanese Patent Application Laid-Open No. 2018-040569 images a well plate (WP) including a plurality of wells (W) that hold specimens and a culture medium (M) therein while holding the well plate (WP) in a holder (12). At this time, the holder (12) abuts against a peripheral edge portion of a lower surface of the well plate (WP) to hold the well plate (WP) in a substantially horizontal attitude. While an illumination part (10) and an imaging part (13) are moved relative to the well plate (WP), each of the wells (W) provided in the well plate (WP) is divided into a plurality of regions and photographed in the plurality of regions.

In general, well plates (WP) are placed one by one in the holder (12) by an operator. In recent years, the well plates (WP) have been placed in the holder (12) by a robot in some cases. After a well plate (WP) is placed in the holder (12), images are acquired by photographing, and specimens are observed or analyzed using the images. In this process, it is essential to observe or analyze the specimens while recognizing the positions of the wells (W) and the specimens themselves in the well plate (WP) in the images. For the purpose of more accurately and easily recognizing the positions of the wells (W) and the specimens themselves in the well plate (WP) in the images, it is hence desirable that the well plate (WP) is aligned and placed in a previously determined position in the holder (12) preparatory to photographing.

SUMMARY OF THE INVENTION

It is therefore an object of the present invention to provide a technique capable of aligning and placing a specimen container in a previously determined position in an imaging device for photographing specimen containers.

To solve the aforementioned problem, a first aspect of the present invention is intended for an imaging device for acquiring an image of a plate-like specimen container having a rectangular shape as seen in top view. The imaging device comprises: a table for placing the specimen container thereon; a position reference member provided on an upper surface of the table and including a first extension and a second extension, the first and second extensions extending in directions intersecting at right angles to each other as seen in top view; a holding mechanism provided on the upper surface of the table and for aligning the specimen container along the position reference member; a movement mechanism for moving the table, the position reference member, and the holding mechanism in a horizontal direction; an illumination part for irradiating the specimen container with light; and an imaging part for photographing the specimen container illuminated by the illumination part, the holding mechanism including a rotating plate extending horizontally in plate-like form, and a main body portion for pivoting the rotating plate forwardly in a circumferential direction around a vertically extending central axis by means of elastic force of a spring, the rotating plate including a front wing portion extending in a radial direction from the central axis, and a protruding portion protruding forwardly in the circumferential direction from the front wing portion, wherein the specimen container is urged in a second direction as seen in top view to align along the first extension when the rotating plate is pivoted forwardly in the circumferential direction to bring the front wing portion into contact with the specimen container, and wherein the specimen container is urged in a first direction as seen in top view to align along the second extension when the rotating plate is pivoted forwardly in the circumferential direction to bring the protruding portion into contact with the specimen container.

A second aspect of the present invention is intended for the imaging device of the first aspect, wherein the rotating plate has a through hole extending through the rotating plate along the central axis, wherein the main body portion includes the spring that is a torsion spring, a fixed shaft passing through the through hole of the rotating plate and extending through a radially inner portion of a coil portion of the spring 91 along the central axis, the fixed shaft being fixed to the table, and a restriction portion for restricting a rearward movement of a first arm portion of the spring in the circumferential direction, and wherein the rotating plate includes an abutment portion in contact with a forward portion of a second arm portion of the spring as seen in the circumferential direction.

A third aspect of the present invention is intended for the imaging device of the first or second aspect, wherein an angle between a first line extending along a forward edge of the front wing portion as seen in the circumferential direction and a second line connecting a forward end point of the protruding portion as seen in the circumferential direction and a point at which the first line contacts the protruding portion is not greater than 135° as seen in top view.

A fourth aspect of the present invention is intended for the imaging device of any one of the first to third aspects, wherein the protruding portion protrudes in a semicircular shape forwardly in the circumferential direction as seen in top view.

A fifth aspect of the present invention is intended for the imaging device of any one of the first to fourth aspects, wherein the rotating plate further includes a rear wing portion extending in a radial direction from the central axis and positioned rearward from the front wing portion in the circumferential direction, and wherein the movement mechanism reciprocally moves the table, the position reference member, and the holding mechanism in a horizontal direction between an imaging position and a retracted position spaced apart from the imaging position, the imaging device further comprising a stopper member coming in contact with the rear wing portion to pivot the rotating plate rearwardly in the circumferential direction around the central axis to thereby release an urging force exerted on the specimen container, when the table, the position reference member, and the holding mechanism move to the retracted position.

A sixth aspect of the present invention is intended for the imaging device of any one of the first to fifth aspects, wherein the specimen container is a well plate including a plurality of specimen storage portions that are recessed portions circular in shape as seen in top view, and wherein liquid is held in the specimen storage portions.

A seventh aspect of the present invention is intended for the imaging device of any one of the first to sixth aspects, wherein the specimen container is placed in a position below the second extension and to the right of the first extension as seen in top view, wherein the specimen container is urged leftwardly as seen in top view to align along the first extension when the rotating plate is pivoted forwardly in the circumferential direction to bring the front wing portion into contact with the specimen container, and wherein the specimen container is urged upwardly as seen in top view to align along the second extension when the rotating plate is pivoted forwardly in the circumferential direction to bring the protruding portion into contact with the specimen container.

According to the first to seventh aspects, even if the specimen container placed on the upper surface of the table is displaced from the first extension or the second extension, the rotating plate of the holding mechanism is pivoted and brought into contact with the specimen container to urge the specimen container, whereby the specimen container is aligned along the first extension and the second extension.

In particular, the imaging device of the third aspect is capable of urging the specimen container with a sufficiently large force in the first direction when the protruding portion is brought into contact with the specimen container while the rotating plate is pivoted.

In particular, the imaging device of the fourth aspect is capable of smoothly changing the position of contact of the protruding portion with the specimen container while pivoting the rotating plate.

In particular, according to the fifth aspect, the table, the position reference member, and the holding mechanism are moved to the retracted position, whereby the rotating plate comes in contact with the stopper member to pivot rearwardly in the circumferential direction. This releases the urging force exerted by the rotating plate on the specimen container. As a result, an operator, a robot, or the like is able to easily perform the operation of replacing the specimen container and the like.

DESCRIPTION OF THE PREFERRED EMBODIMENTS

Figure 1:
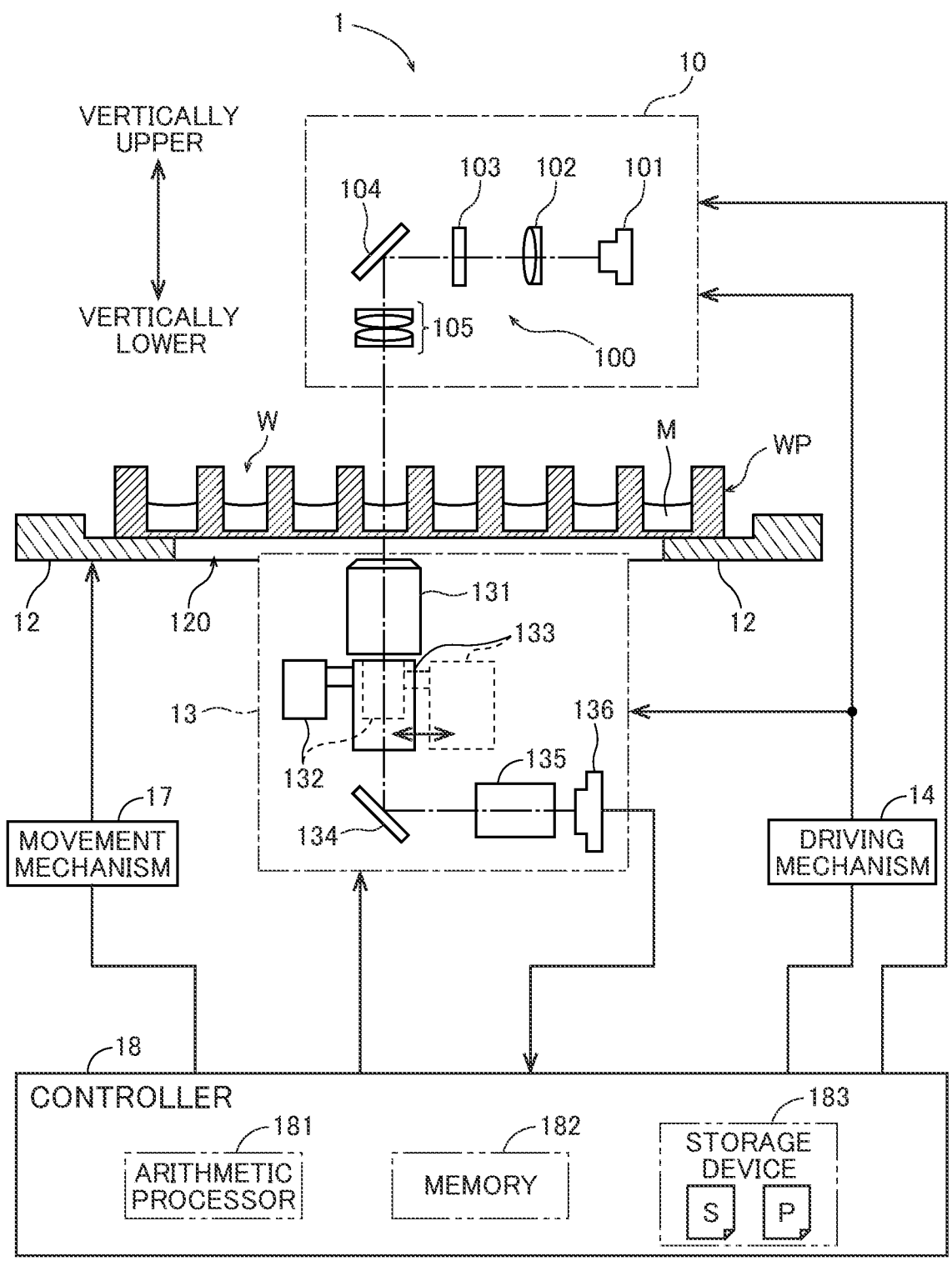
FIG. 1 is a diagram schematically showing a configuration of an imaging device.

A preferred embodiment according to the present invention will now be described with reference to the drawings.
<1. Configuration of Imaging Device>
FIG. 1 is a diagram schematically showing a configuration of an imaging device 1 according to one preferred embodiment of the present invention. This imaging device 1 is a device for photographing specimens such as cells, cell colonies, and bacteria being cultured in a liquid put into wells W formed in an upper surface of a well plate WP. These cells, cell colonies, bacteria, and the like are collectively referred to hereinafter as "cells and the like".

The well plate WP has a flat three-dimensional shape with a rectangular shape as seen in top view (with reference to FIG. 2 to be described later). The expression "seen in top view" means "seen vertically from above" hereinafter. A "top surface or upper surface" means a "vertically topside surface" hereinafter. The well plate WP is made of, for example, a transparent resin permeable to light. The well plate WP includes the wells W arranged in a regular pattern and serving as specimen storage portions each having an opening on the upper surface side and a transparent bottom surface on the lower surface side. The well plate WP includes an array with 6, 24, 96, or 384 wells W, for example. An instance in which the well plate WP is used as a specimen container will be given below for description. However, the present invention is not limited to this. A dish or a container known as a petri dish (a container having only a single specimen storage portion) may be used as the specimen container. That is, a container having only a single specimen storage portion may be used.

Each of the wells W is typically a recessed portion circular in shape as seen in top view and having a flat bottom surface. However, the shape of the wells W is not limited to this. The wells W have a diameter and a depth both generally on the order of several millimeters to several tens of millimeters. Each of the wells W holds a predetermined amount of liquid (culture solution) serving as a culture medium M that provides a growth environment for cells and the like. The amount of liquid held in each of the wells W is generally on the order of 50 to 200 microliters. The cells and the like cultured in the liquid under predetermined culturing conditions are objects to be imaged.

The imaging device 1 is used, for example, in a screening step for narrowing down compounds that are candidates for medical and pharmaceutical products in the fields of research and development of medical and pharmaceutical products. A person responsible for the screening step adds compounds of different concentrations and compositions to the plurality of wells W of the well plate WP. Then, the person acquires image data about the cells and the like in the wells W of the well plate WP in the imaging device 1. Thereafter, the person compares and analyzes the culture states of the cells and the like, based on the acquired image data, to verify the efficacy of the compounds added to the culture solution. However, the imaging device 1 may be used to observe cell differentiation and the like in the research and development of pluripotent stem cells such as iPS cells or ES cells.

Figure 2:
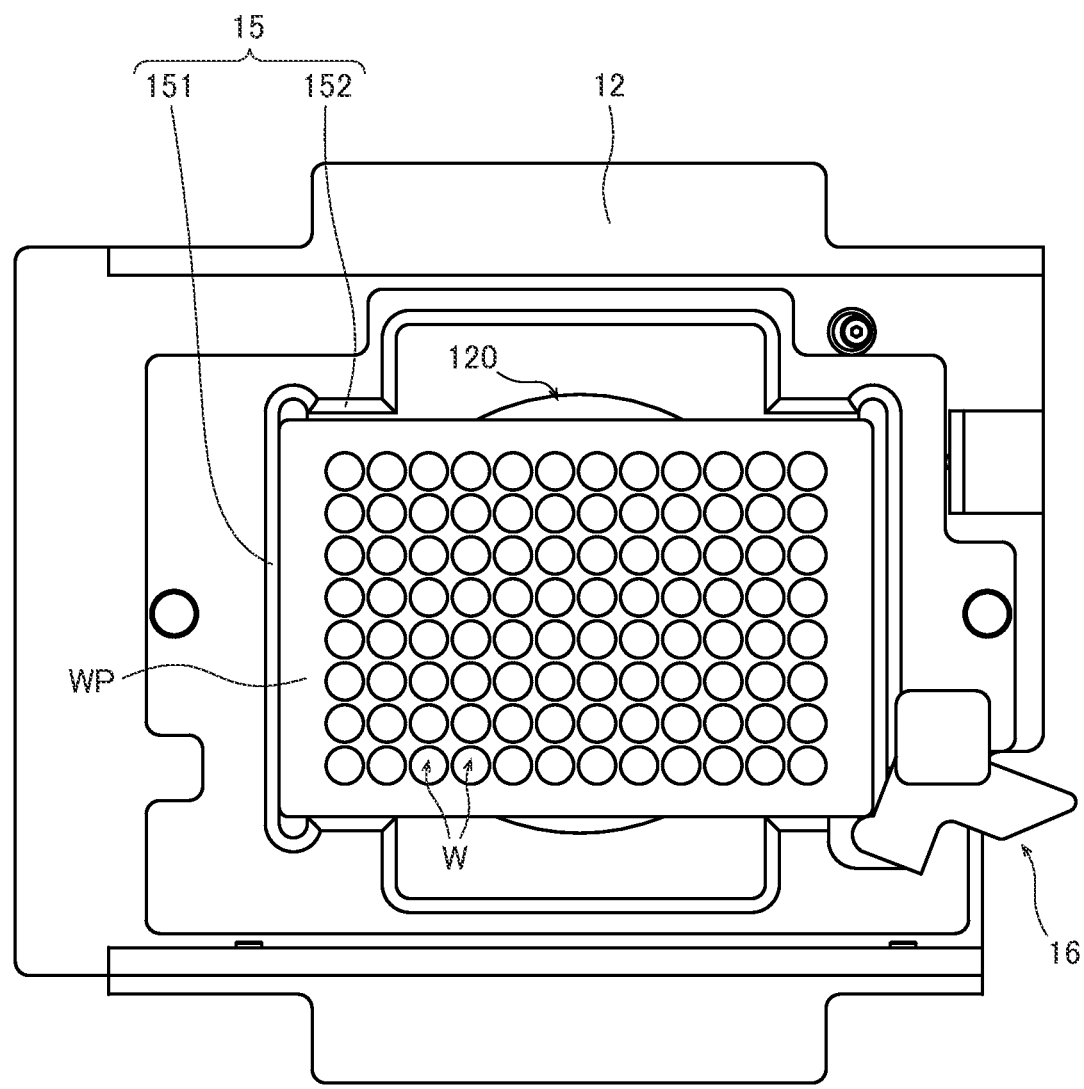
FIG. 2 is a top view of a table, a position reference member, a holding mechanism, and a well plate in the imaging device.
Figure 2:
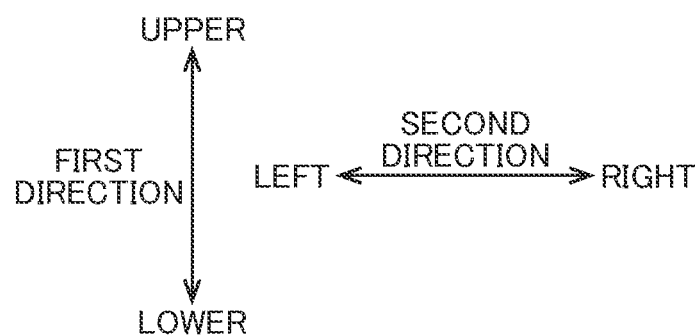

FIG. 2 is a top view of a table 12 to be described later, a position reference member 15 to be described later, a holding mechanism 16 to be described later, and the well plate WP placed on the table 12 in the imaging device 1. As shown in FIGS. 1 and 2, this imaging device 1 includes an illumination part 10, the table 12, an imaging part 13, a driving mechanism 14, the position reference member 15, the holding mechanism 16, a movement mechanism 17, and a controller 18. The illumination part 10 is disposed in a vertically upper portion of this imaging device 1. The table 12 is disposed vertically below the illumination part 10, and the imaging part 13 is disposed vertically below the table 12.

The illumination part 10 emits light for imaging to the well plate WP. The illumination part 10 has a single illumination optical system 100 including a light source 101 such as a white LED (Light Emitting Diode), a collector lens 102, a diffusion plate 103, a reflecting mirror 104, and a condenser lens 105. During photography, the light source 101 is controlled by the controller 18 to emit light. The light emitted from the light source 101 passes through the collector lens 102 and enters the diffusion plate 103. The direction of travel of a light beam exiting the diffusion plate 103 is changed to a vertically downward direction by the reflecting mirror 104. The light beam changed in direction of travel to the vertically downward direction passes through the condenser lens 105 and exits the illumination part 10 downwardly. The light exiting the illumination part 10 enters the wells W from above the well plate WP placed on the table 12 to illuminate objects to be imaged in the wells W. However, the configuration of the illumination part 10 is not limited to this. The illumination part 10 is required only to apply light from the opposite side of the imaging part 13 toward the well plate WP.

When the imaging device 1 performs the imaging, the well plate WP including the plurality of wells W holding the specimens and the culture medium M is placed on an upper surface of the table 12. The table 12 extends horizontally in plate-like form. A photographing hole 120 circular in shape as seen in top view is provided in the center of the table 12. The photographing hole 120 extends vertically through the table 12. When the well plate WP is placed on the upper surface of the table 12 so as to straddle the photographing hole 120, a vertically lower surface of the central portion of the well plate WP is exposed. The table 12 abuts against a peripheral portion of the vertically lower surface of the well plate WP to hold the well plate WP in a substantially horizontal attitude. The detailed structures of the table 12, the position reference member 15, and the holding mechanism 16 will be described later.

The imaging part 13 photographs the well plate WP illuminated by the illumination part 10 to image the specimens (cells and the like) in the wells W. The imaging part 13 includes an objective lens 131, an afocal system for low magnification 132, an afocal system for high magnification 133, a reflecting mirror 134, the image-forming lens 135, and an imaging element 136. The objective lens 131 is disposed in a position vertically directly below the well plate WP. The objective lens 131 has an optical axis directed vertically and coaxial with the optical axis of the illumination optical system 100. Light emitted from the illumination part 10 and entering the liquid (the culture medium M) from vertically above the wells W illuminates the objects to be imaged, and light transmitted vertically downwardly through the bottom surfaces of the wells W enters the objective lens 131.

The afocal system for low magnification 132 and the afocal system for high magnification 133 are provided in switchable fashion vertically below the objective lens 131. During the imaging, one of the afocal system for low magnification 132 and the afocal system for high magnification 133 is selectively disposed in a position vertically directly below the objective lens 131. Light exiting the afocal system (the afocal system for low magnification 132 or the afocal system for high magnification 133) is reflected by the reflecting mirror 134. Thereafter, the light passes through the image-forming lens 135 and enters the imaging element 136.

The imaging element 136 is an area image sensor having a two-dimensional light receiving surface. A CCD sensor, a CMOS sensor, or the like may be used as the imaging element 136. The imaging element 136 images an object that is image-formed on the light receiving surface of the imaging element 136 by the image-forming lens 135. The imaging element 136 converts an optical image of received light into an electrical signal to output the electrical signal as an image signal. Such an imaging method allows noncontact, nondestructive, and noninvasive imaging of the cells and the like which are objects to be imaged, to thereby suppress damages to the cells and the like due to the imaging. The operations of the components of the imaging part 13 are controlled by the controller 18. The image signal is inputted from the imaging part 13 to the controller 18.

During the imaging, the driving mechanism 14 is controlled by the controller 18 to move the illumination part 10 and the imaging part 13. The driving mechanism 14 moves the illumination part 10 horizontally. Also, the driving mechanism 14 moves the imaging part 13 horizontally or vertically. In the imaging device 1, the positional relationship between the illumination part 10 and the imaging part 13 is determined so that the center of the light exiting the illumination part 10 substantially coincides with the optical axis of the objective lens 131. Thus, when moving the imaging part 13 horizontally, the driving mechanism 14 moves the illumination part 10 and the imaging part 13 integrally. This allows a good illumination condition to be maintained when the imaging is performed in any position of any of the wells W.

Figure 3:
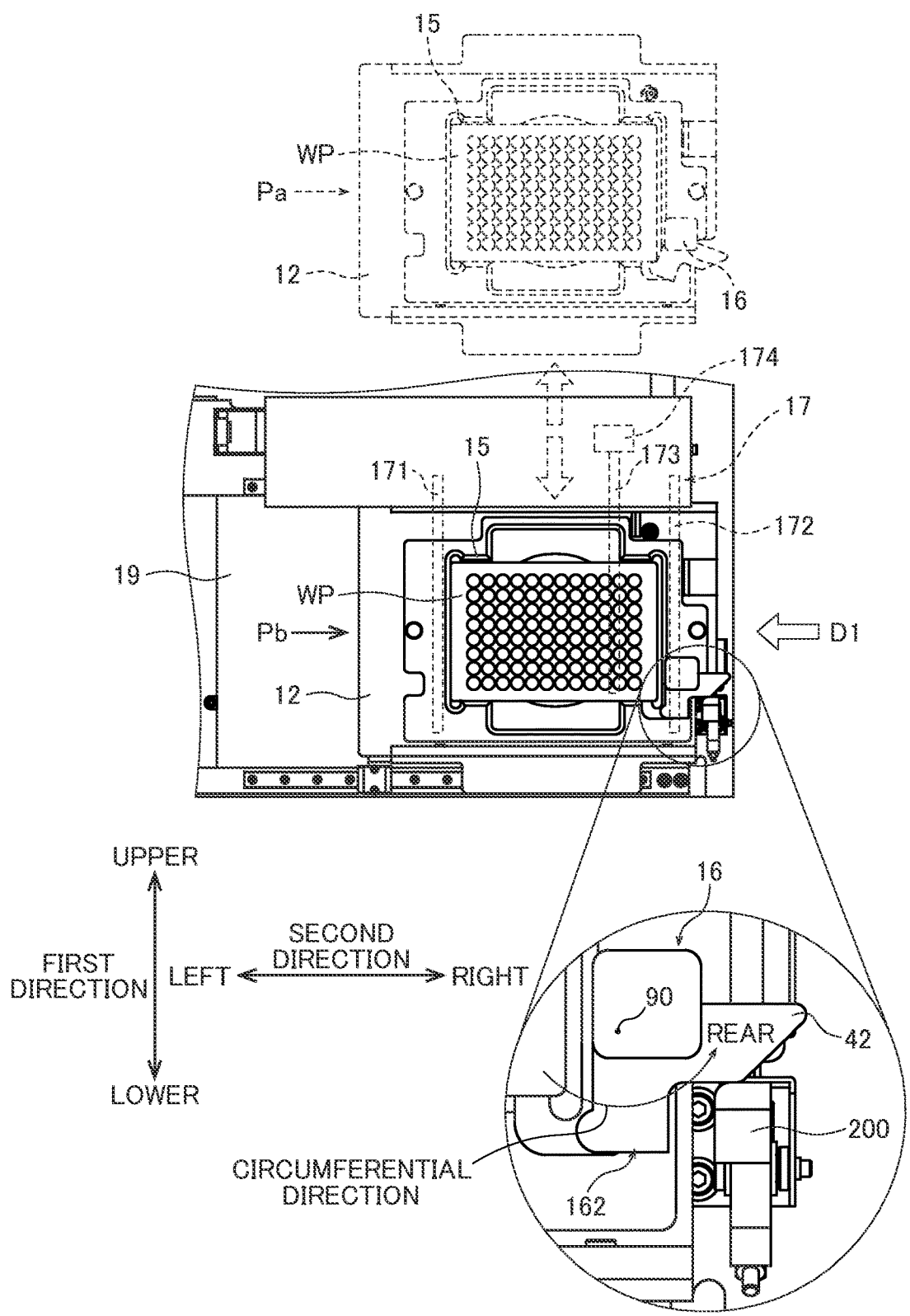
FIG. 3 is a top view of the table and its surroundings in the imaging device.

The movement mechanism 17 is a device for moving the table 12, the position reference member 15, and the holding mechanism 16 horizontally. FIG. 3 is a top view of the table 12 and its surroundings in the imaging device 1. As shown in FIG. 3, the movement mechanism 17 reciprocally moves the table 12, the position reference member and the holding mechanism 16 which are both fixed to the upper surface of the table 12, and the well plate WP placed on the upper surface of the table 12 horizontally between an imaging position Pa and a retracted position Pb. The retracted position Pb is a position spaced apart from the imaging position Pa. In FIG. 3, the table 12, the position reference member 15, the holding mechanism 16, and the well plate WP which are in the imaging position Pa are shown in broken lines. It should be noted that the imaging position Pa is shown as more largely spaced apart from the retracted position Pb than in reality for further clarity of illustration in FIG. 3.

Figure 4:
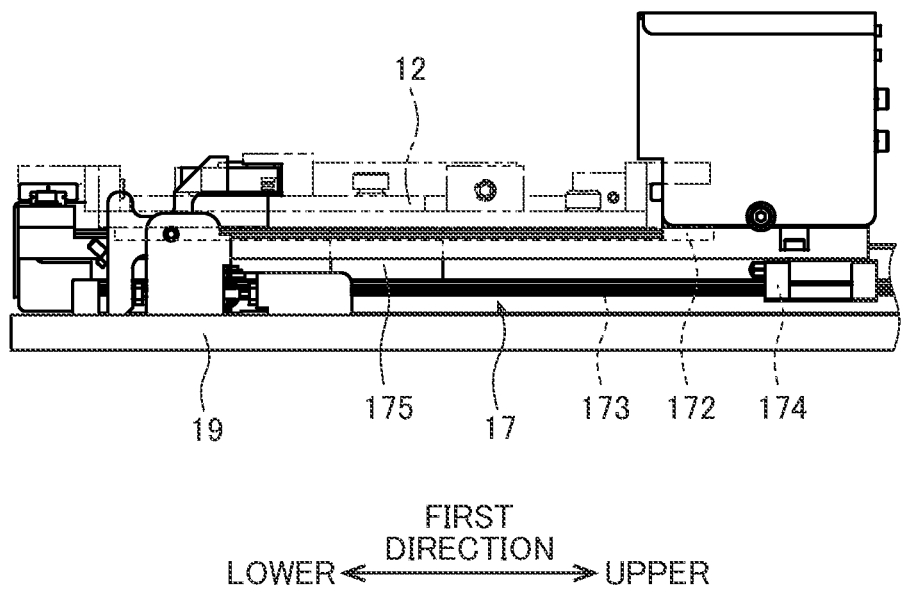
FIG. 4 is a side view of the table and its surroundings in the imaging device as seen in the direction of a solid hollow arrow in FIG. 3.

FIG. 4 is a side view of the table 12 and its surroundings in the imaging device 1 as seen in the direction of a solid hollow arrow D1 in FIG. 3. The table 12 is shown in dash-double-dot lines in FIG. 4. As shown in FIGS. 3 and 4, the imaging device 1 further includes a support frame 19.

The support frame 19 supports the table 12 and the movement mechanism 17 in a substantially horizontal attitude from vertically below. The movement mechanism 17 includes a pair of linear guides 171 and 172, a ball screw 173, and a motor 174. The pair of linear guides 171 and 172, the ball screw 173, and the motor 174 are disposed on an upper surface of the support frame 19.

As shown in FIGS. 3 and 4, each of the linear guides 171 and 172 is disposed so as to extend in a first direction as seen in top view. The table 12 moves along the pair of linear guides 171 and 172 to thereby move in the first direction as seen in top view. The ball screw 173 extends in the first direction as seen in top view, and is disposed between the linear guides 171 and 172. The ball screw 173 is connected to the motor 174, and is driven by the motor 174 to rotate. The table 12 is coupled to the ball screw 173 via a coupling member 175, and is moved along the pair of linear guides 171 and 172 by the rotation of the ball screw 173.

The controller 18 is a control means for controlling the operations of the components of the imaging device 1. The controller 18 is electrically connected to the illumination part 10, the imaging part 13, the driving mechanism 14, and the movement mechanism 17. The controller 18 is formed by a computer including an arithmetic processor 181 such as a CPU, a memory 182, and a storage device 183. The controller 18 controls the operations of the aforementioned components, based on a preset operating sequence S and parameters P which are stored in the storage device 183, and input signals from the outside.

Specifically, the controller 18 operates the driving mechanism 14 to thereby move the imaging part 13 horizontally or vertically. By moving the imaging part 13 horizontally, the imaging part 13 moves horizontally with respect to the wells W. By moving the imaging part 13 vertically, focus adjustment is performed. The controller 18 also operates the driving mechanism 14 to thereby move the illumination part 10 horizontally. The controller 18 turns on the light source 101 in accordance with the position of imaging. Also, the controller 18 controls the operation of the imaging part 13 to photograph the well plate WP, and receives an image signal (analog data) from the imaging element 136 to convert the image signal into digital image data.

The controller 18 operates the movement mechanism 17 to reciprocally move the table 12, the position reference member 15 and the holding mechanism 16 which are both fixed to the upper surface of the table 12, and the well plate WP placed on the upper surface of the table 12 horizontally between the imaging position Pa and the retracted position Pb. However, the illumination part 10, the imaging part 13, the driving mechanism 14, and the movement mechanism 17 may be disconnected from the controller 18 and manually operated by an operator, a robot, or the like.

<2. Detailed Structures of Table, Position Reference Member, and Holding Mechanism>

Next, the detailed structures of the table 12, the position reference member 15, and the holding mechanism 16 will be described. As mentioned above, the well plate WP is placed on the table 12 by an operator, a robot, or the like in the process using the imaging device 1. While the illumination part 10 and the imaging part 13 are moved with respect to the well plate WP that is stationary, the well plate WP is then photographed. The specimens are observed or analyzed using images acquired by the photographing. In this process, it is essential to observe or analyze the specimens while recognizing the positions of the wells W and the specimens themselves in the well plate WP in the images. For the purpose of more accurately and easily recognizing the positions of the wells W and the specimens themselves in the well plate WP in the images, it is hence desirable that the well plate WP is aligned and placed in a previously determined position on the upper surface of the table 12 preparatory to the photographing.

As shown in FIG. 2, the position reference member 15 protruding vertically upwardly is provided on the upper surface of the table 12. The position reference member may be formed integrally with the table 12. The position reference member 15 is provided so as to surround the outside of the well plate WP as seen in top view. The position reference member 15 forms a reference position for aligning and placing the well plate WP in a previously determined position on the upper surface of the table 12. The position reference member 15 includes a first extension 151 and a second extension 152. The first extension 151 extends in the first direction in the left side position of the table 12 as seen in top view. The second extension 152 extends in a second direction in the upper left side position of the table 12 as seen in top view. The first extension 151 and the second extension 152 extend in the directions intersecting at right angles to each other as seen in top view. In the present preferred embodiment, the well plate WP is placed below the second extension 152 and to the right of the first extension 151 on the upper surface of the table 12 as seen in top view.

Figure 5:
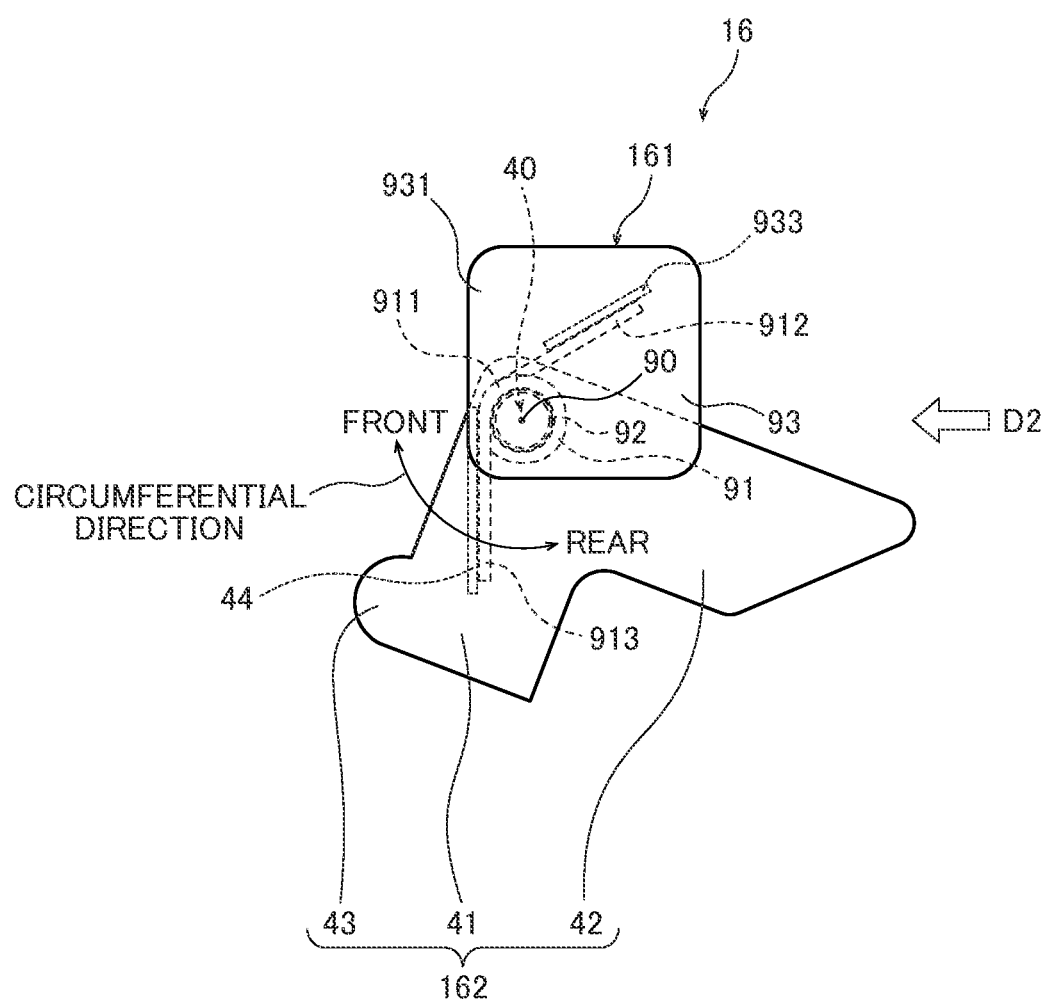
FIG. 5 is a top view of the holding mechanism.
Figure 6:
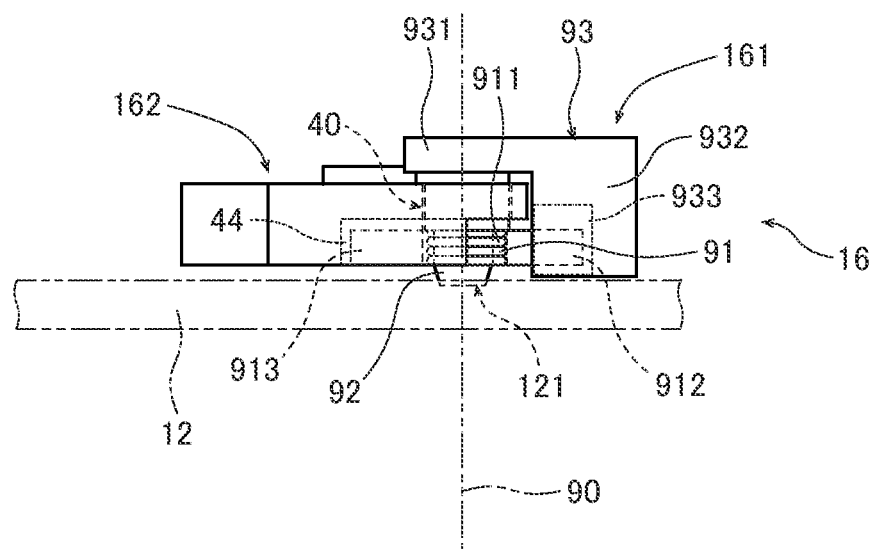
FIG. 6 is a side view of the holding mechanism as seen in the direction of a solid hollow arrow in FIG. 5.

As shown in FIG. 2, the holding mechanism 16 is provided in the lower right position of the upper surface of the table 12 as seen in top view. The holding mechanism 16 is a mechanism for aligning the well plate WP along the position reference member 15. FIG. 5 is a top view of the holding mechanism 16. FIG. 6 is a side view of the holding mechanism 16 as seen in the direction of a solid hollow arrow D2 in FIG. 5. The table 12 is shown in dash-double-dot lines in FIG. 6. As shown in FIGS. 5 and 6, the holding mechanism 16 includes a main body portion 161 and a rotating plate 162.

The main body portion 161 includes a spring 91, a fixed shaft 92, and a cover 93. As shown in broken lines in FIG. 5, the spring 91 in the present preferred embodiment is a torsion spring. The spring 91 includes a coil portion 911, a first arm portion 912, and a second arm portion 913. The coil portion 911 is disposed along a vertically extending central axis 90. A direction orthogonal to the central axis 90 is referred to hereinafter as a "radial direction". A direction along an arc around the central axis 90 is referred to hereinafter as a "circumferential direction".

The fixed shaft 92 is a member extending in columnar form along the central axis 90. For example, a screw is used for the fixed shaft 92 of the present preferred embodiment. The fixed shaft 92 extends along the central axis 90 inside the coil portion 911 of the spring 91 as seen in the radial direction. The fixed shaft 92 is fastened and fixed to a threaded hole 121 provided in the table 12. This allows the spring 91 to rotate around the central axis 90.

The cover 93 is fixed to the upper surface of the table 12 with the use of a mechanism not shown. The cover 93 includes an upper cover portion 931 and a side cover portion 932. The upper cover portion 931 covers the fixed shaft 92 from vertically above. The side cover portion 932 covers part of the side surfaces of the spring 91 and the fixed shaft 92. The side cover portion 932 is provided with a restriction portion 933. The restriction portion 933 extends, for example, vertically in the form of a wall. The first arm portion 912 of the spring 91 is fixed to the restriction portion 933. This restricts the circumferentially rearward movement of the first arm portion 912 of the spring 91. In other words, this restricts the counterclockwise movement of the first arm portion 912 of the spring 91 around the central axis 90 as seen in top view. However, the restriction portion 933 need not necessarily be fixed to the first arm portion 912 of the spring 91. The restriction portion 933 may abut against the circumferential rear of the first arm portion 912 of the spring 91 to prevent the circumferentially rearward movement of the first arm portion 912.

Figure 7:
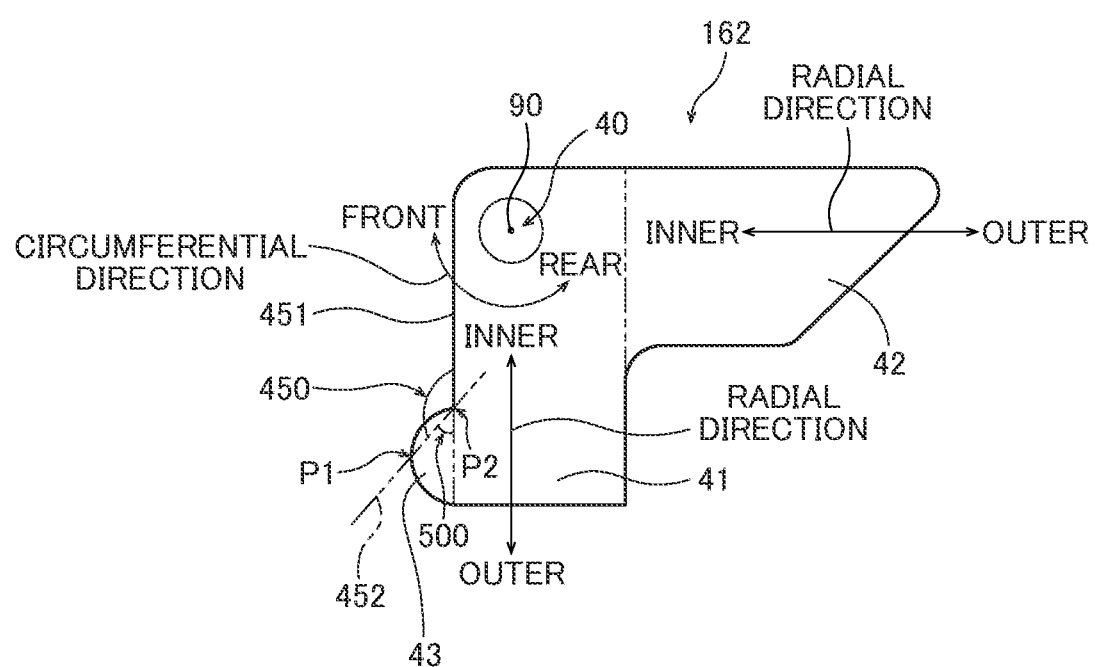
FIG. 7 is a top view of a rotating plate.

The rotating plate 162 is a member extending horizontally in plate-like form. FIG. 7 is a top view of the rotating plate 162. As shown in FIG. 7, the rotating plate 162 includes a front wing portion 41, a rear wing portion 42, and a protruding portion 43. The front wing portion 41 is a portion extending in a radial direction from the central axis 90. The rear wing portion 42 extends in a radial direction from the central axis 90 and is positioned circumferentially rearward from the front wing portion 41. In other words, the rear wing portion 42 is in a position leading the front wing portion 41 in a counterclockwise direction around the central axis 90 as seen in top view. The rear wing portion 42 extends in wing-like form rearwardly in the circumferential direction from the front wing portion 41 as seen in top view. The protruding portion 43 protrudes forwardly in the circumferential direction from the front wing portion 41. In other words, the protruding portion 43 protrudes from the front wing portion 41 in a clockwise direction around the central axis 90 as seen in top view. The protruding portion 43 protrudes forwardly in the circumferential direction from a radially outer portion of the front wing portion 41. In the present preferred embodiment, the protruding portion 43 protrudes in a semicircular shape forwardly in the circumferential direction as seen in top view. However, the protruding portion 43 may protrude in a polygonal shape, such as a triangular or rectangular shape, forwardly in the circumferential direction as seen in top view.

The rotating plate 162 is provided with a through hole 40. The through hole 40 extends through the rotating plate 162 along the central axis 90. In the present preferred embodiment, the through hole 40 extends through a radially inner portion of the front wing portion 41 along the central axis 90. As shown in FIG. 6, the rotating plate 162 is disposed, with a portion thereof near the through hole 40 sandwiched between the upper cover portion 931 of the main body portion 161 and the table 12. The fixed shaft 92 is inserted through the radial inside of the through hole 40. Specifically, the fixed shaft 92 passes through the through hole 40 of the rotating plate 162, extends through a radially inner portion of the coil portion 911 of the spring 91 along the central axis 90, and is fixed to the table 12. This allows the rotating plate 162 to rotate around the central axis 90.

As shown in FIGS. 5 and 6, the rotating plate 162 is further provided with an abutment portion 44. The abutment portion 44 extends, for example, vertically in the form of a wall. With the rotating plate 162 sandwiched between the upper cover portion 931 of the main body portion 161 and the table 12 and fixed to the table 12 via the fixed shaft 92, the abutment portion 44 contacts a circumferentially forward portion of the second arm portion 913 of the spring 91. In other words, the abutment portion 44 contacts a portion of the second arm portion 913 of the spring 91 which is leading in a clockwise direction around the central axis 90 as seen in top view. The second arm portion 913 of the spring 91 may be fixed to the abutment portion 44.

As mentioned above, the circumferentially rearward movement of the first arm portion 912 of the spring 91 is restricted by the restriction portion 933. In other words, the counterclockwise movement of the first arm portion 912 of the spring 91 around the central axis 90 as seen in top view is restricted. Thus, the second arm portion 913 is pressed forwardly in the circumferential direction by the elastic force of the pair of arm portions 912 and 913 which tends to move away from each other outwardly in the circumferential direction. In other words, the second arm portion 913 is pressed in a clockwise direction around the central axis 90 as seen in top view. As described above, the abutment portion 44 of the rotating plate 162 contacts the circumferentially forward portion of the second arm portion 913. Thus, the rotating plate 162 including the abutment portion 44 together with the second arm portion 913 of the spring 91 is pressed forwardly in the circumferential direction to thereby pivot forwardly in the circumferential direction. In the present preferred embodiment, a structure is formed in which the rotating plate 162 is pivoted forwardly in the circumferential direction around the vertically extending central axis 90 by the elastic force of the spring 91 which is a torsion spring.

With reference to FIG. 7, a line extending along a circumferentially forward edge of the front wing portion 41 as seen in top view is referred to hereinafter as a "first line 451". A line connecting a circumferentially forward end point P1 of the protruding portion 43 and a point P2 is referred to hereinafter as a "second line 452". The point P2 is a point at which the first line 451 contacts the protruding portion 43. In the present preferred embodiment, the angle 450 between the first line 451 and the second line 452 as seen in top view is, for example, not greater than 135°. When the angle between the extension of the first line 451 and the second line 452 is defined as a "protrusion angle 500 of the protruding portion 43 from the front wing portion 41", the protrusion angle 500 is greater than 45°. In other words, the protruding portion 43 protrudes at a sufficient angle forwardly in the circumferential direction from the front wing portion 41.

Figure 8:
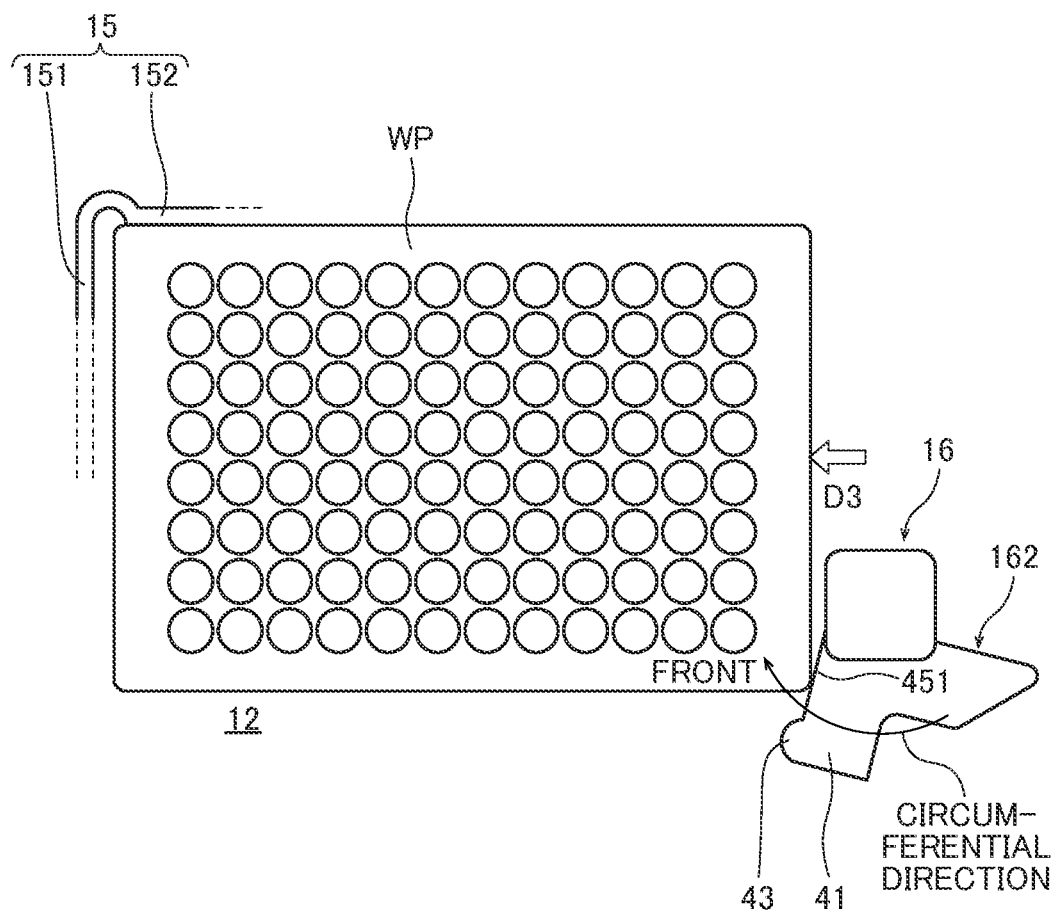
FIGS. 8, 9, and 10 are views for illustrating the position of the well plate placed on the table and the operation by the holding mechanism.
Figure 8:
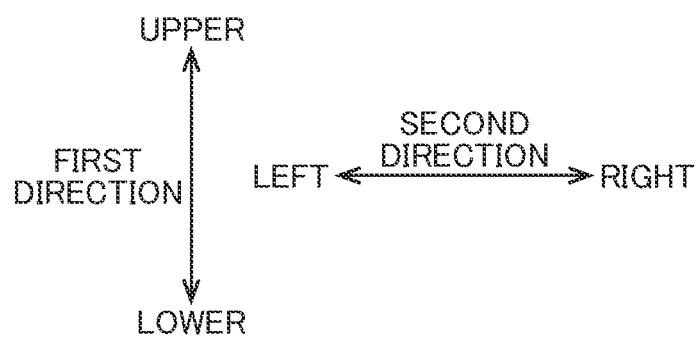
Figure 9:
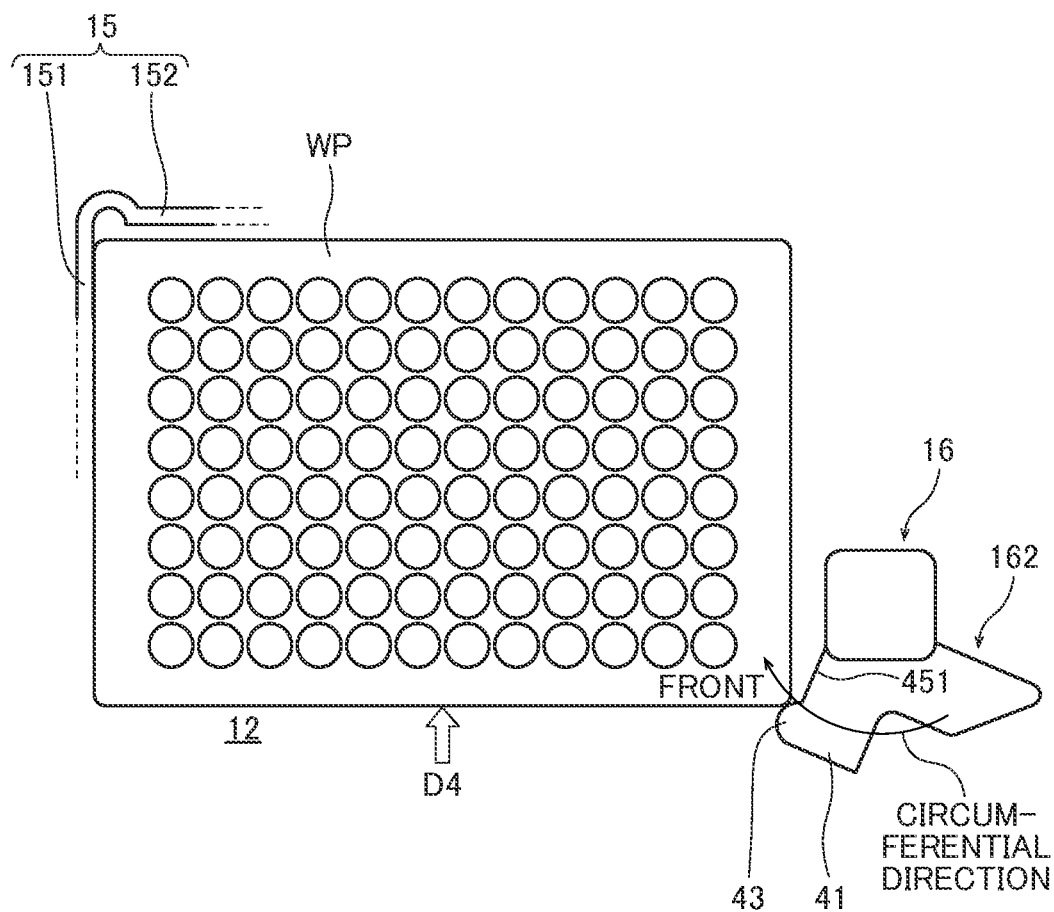
Figure 9:
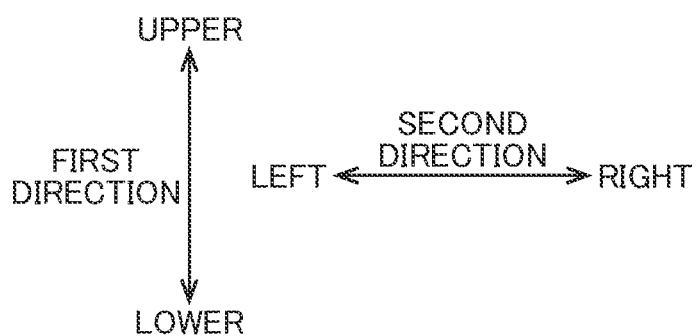
Figure 10:
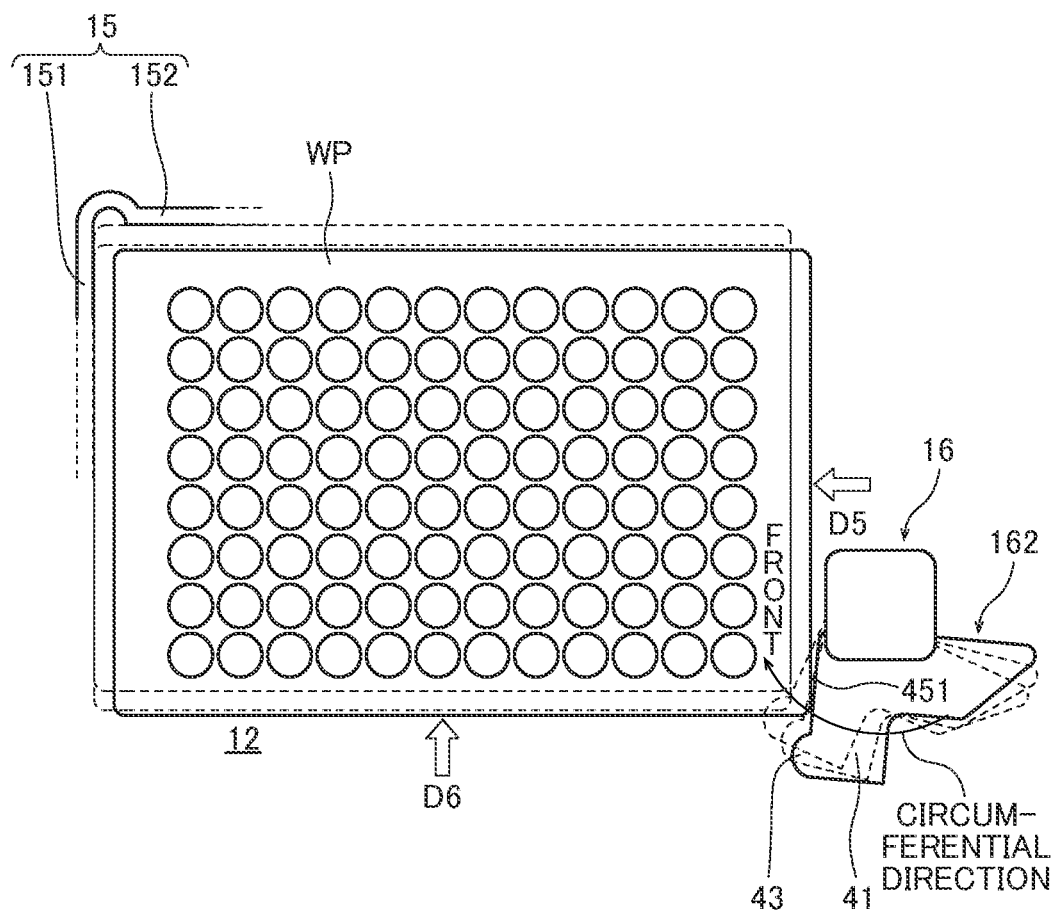
Figure 10:
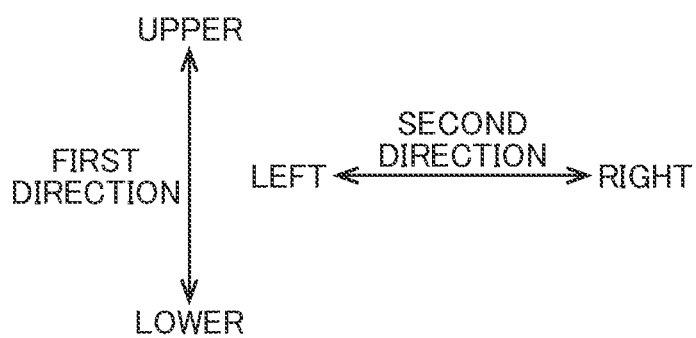

FIGS. 8 to 10 are views for illustrating the position of the well plate WP placed on the table 12 and the operation by the holding mechanism 16. In FIG. 8, a case is assumed in which the well plate WP is displaced to the right side with respect to the position reference member 15 as seen in top view when the well plate WP is placed on the table 12 by an operator, a robot, or the like. In this case, the rotating plate 162 is pivoted forwardly in the circumferential direction, so that the first line 451 of the front wing portion 41 comes in contact with the well plate WP to urge the well plate WP leftwardly. This causes the well plate WP to move on the upper surface of the table 12 in the direction of a solid hollow arrow D3 to thereby align along the first extension 151. In the present preferred embodiment, when the rotating plate 162 is pivoted forwardly in the circumferential direction to bring the front wing portion 41 into contact with the well plate WP, the well plate WP is urged leftwardly as seen in top view to thereby align along the first extension 151.

In FIG. 9, a case is assumed in which the well plate WP is displaced to the lower side with respect to the position reference member 15 as seen in top view when the well plate WP is placed on the table 12 by an operator, a robot, or the like. In this case, the rotating plate 162 is pivoted forwardly in the circumferential direction, so that the protruding portion 43 comes in contact with the well plate WP to urge the well plate WP upwardly. As described above, the protruding portion 43 protrudes at a sufficient angle forwardly in the circumferential direction from the front wing portion 41. Thus, when the rotating plate 162 is pivoted to come in contact with the well plate WP, the protruding portion 43 is convex upwardly as seen in top view to be able to urge the well plate WP with a sufficiently large force in the first direction. This causes the well plate WP to move on the upper surface of the table 12 in the direction of a solid hollow arrow D4 to thereby align along the second extension 152. In the present preferred embodiment, when the rotating plate 162 is pivoted forwardly in the circumferential direction to bring the protruding portion 43 into contact with the well plate WP, the well plate WP is urged upwardly as seen in top view to thereby align along the second extension 152.

As described above, the protruding portion 43 of the present preferred embodiment protrudes in a semicircular shape forwardly in the circumferential direction as seen in top view. This allows the protruding portion 43 to smoothly change the position of contact with the well plate WP when the rotating plate 162 is pivoted.

In FIG. 10, a case is assumed in which the well plate WP is displaced to the lower right side with respect to the position reference member 15 as seen in top view when the well plate WP is placed on the table 12 by an operator, a robot, or the like. In this case, the rotating plate 162 is pivoted forwardly in the circumferential direction, so that the first line 451 of the front wing portion 41 initially comes in contact with the well plate WP to urge the well plate WP leftwardly. This causes the well plate WP to move on the upper surface of the table 12 in the direction of a solid hollow arrow D5 to thereby align along the first extension 151. Next, the rotating plate 162 is further pivoted forwardly in the circumferential direction, so that the position of contact between the rotating plate 162 and the well plate WP is displaced downwardly as seen in top view on the first line 451 of the front wing portion 41. Then, the protruding portion 43 comes in contact with the well plate WP to urge the well plate WP upwardly. This causes the well plate WP to move on the upper surface of the table 12 in the direction of a solid hollow arrow D6 to thereby align along the second extension 152. As a result, the well plate WP is disposed along both the first extension 151 and the second extension 152. In other words, the well plate WP is disposed in a previously determined reference position on the upper surface of the table 12.

As shown in FIG. 3, a stopper member 200 is further disposed on the upper surface of the support frame 19. The stopper member 200 protrudes vertically upwardly from the upper surface of the support frame 19. The stopper member 200 is provided in the vicinity of the retracted position Pb of the support frame 19 as seen in top view. When the table 12, the position reference member 15 and the holding mechanism 16 which are both fixed to the upper surface of the table 12, and the well plate WP placed on the upper surface of the table 12 are moved to the retracted position Pb by the operation of the movement mechanism 17, the stopper member 200 comes in contact with the rear wing portion 42 of the rotating plate 162. This presses the rear wing portion 42 in the direction opposite to the direction of the movement of the holding mechanism 16. As a result, the rotating plate 162 including the rear wing portion 42 is pivoted rearwardly in the circumferential direction around the central axis 90 against the elastic force of the spring 91. In other words, the rotating plate 162 is pivoted in a counterclockwise direction around the central axis 90 as seen in top view. Thus, the rotating plate 162 is separated from the well plate WP, so that the urging force exerted by the rotating plate 162 on the well plate WP is released. As a result, an operator, a robot, or the like is able to easily move the well plate WP and easily perform the operation of replacing the well plate WP and the like.

<3. Procedure for Entire Process>

Next, an outline of a procedure for the entire process using the imaging device 1 will be described.

First, an operator, a robot, or the like places the well plate WP on the upper surface of the table 12 lying in the retracted position Pb in the imaging device 1. At this time, the rotating plate 162 of the holding mechanism 16 does not interfere with the well plate WP because the rotating plate 162 is pivoted rearwardly in the circumferential direction around the central axis 90 by the stopper member 200. The well plate WP is placed in a position below the second extension 152 and to the right of the first extension 151 on the upper surface of the table 12 as seen in top view. At that time, there are cases in which the well plate WP is displaced from the second extension 152 or the first extension 151.

Next, the imaging device 1 operates the movement mechanism 17 to move the table 12, the position reference member 15 and the holding mechanism 16 which are both fixed to the upper surface of the table 12, and the well plate WP placed on the upper surface of the table 12 toward the imaging position Pa. Then, the rotating plate 162 is separated from the stopper member 200 and pivoted forwardly in the circumferential direction around the central axis 90 by the elastic force of the spring 91. The rotating plate 162 comes in contact with the well plate WP to urge the well plate WP upwardly and leftwardly. Thus, even if the well plate WP placed on the upper surface of the table 12 is initially displaced from the second extension 152 or the first extension 151, the well plate WP is urged by the rotating plate 162 to move, thereby aligning along the first extension 151 and the second extension 152. In other words, the well plate WP is aligned in a previously determined reference position on the upper surface of the table 12.

Subsequently, while operating the driving mechanism 14 to move the illumination part 10 and the imaging part 13, the imaging device 1 divides each of the wells W provided in the well plate WP into a plurality of regions and photographs the plurality of regions. In other words, the imaging device 1 acquires images of the well plate WP. Upon completion of the photographing of the entire well plate WP placed on the upper surface of the table 12, the imaging device 1 operates the movement mechanism 17 again to move the table 12, the position reference member 15 and the holding mechanism 16 which are both fixed to the upper surface of the table 12, and the well plate WP placed on the upper surface of the table 12 toward the retracted position Pb. Then, the rotating plate 162 comes in contact with the stopper member 200 again to pivot rearwardly in the circumferential direction around the central axis 90. This separates the rotating plate 162 from the well plate WP, so that the urging force exerted by the rotating plate 162 on the well plate WP is released. Then, an operator, a robot, or the like is able to replace the well plate WP with a new one and perform the aforementioned process again.

<4. Modifications>

While the preferred embodiment according to the present invention has been described hereinabove, the present invention is not limited to the aforementioned preferred embodiment.

In the aforementioned preferred embodiment, the position reference member 15 is provided on the upper left side of the well plate WP as seen in top view, and forms the reference position for aligning the well plate WP in the previously determined position on the upper surface of the table 12. The holding mechanism 16 is provided on the lower right side of the well plate WP as seen in top view, and has a structure for aligning the well plate WP in the reference position. However, the reference position for aligning the well plate WP need not necessarily be on the upper left side as seen in top view.

Specifically, the present invention is required only to be configured such that the well plate WP is urged in the second direction as seen in top view to thereby align along the first extension 151 when the rotating plate 162 is pivoted forwardly in the circumferential direction to bring the front wing portion 41 into contact with the well plate WP. Also, the present invention is required only to be configured such that the well plate WP is urged in the first direction as seen in top view to thereby align along the second extension 152 when the rotating plate 162 is pivoted forwardly in the circumferential direction to bring the protruding portion 43 into contact with the well plate WP. This allows the rotating plate 162 to contact and urge the well plate WP while being pivoted, thereby aligning the well plate WP along the first extension 151 and the second extension 152, even if the well plate WP is displaced from the first extension 151 or the second extension 152.

In the aforementioned preferred embodiment, the well plate WP is rectangular in shape as seen in top view. However, the shape of the well plate WP is not limited to this. The well plate WP is required only to have a shape with a corner for aligning with a position reference member having a polygonal shape for forming a previously determined reference position as seen in top view.

The configuration of the details in the device may differ from that shown in the figures of the present invention. The components described in the aforementioned preferred embodiment and in the modifications may be combined together, as appropriate, without inconsistencies.

While the invention has been shown and described in detail, the foregoing description is in all aspects illustrative and not restrictive. It is therefore understood that numerous modifications and variations can be devised without departing from the scope of the invention.

What is claimed is:

1. An imaging device for acquiring an image of a plate-like specimen container having a rectangular shape as seen in top view, comprising:
   a table for placing said specimen container thereon;
   a position reference member provided on an upper surface of said table and including a first extension and a second extension, said first and second extensions extending in directions intersecting at right angles to each other as seen in top view;
   a holding mechanism provided on the upper surface of said table and for aligning said specimen container along said position reference member;
   a movement mechanism for moving said table, said position reference member, and said holding mechanism in a horizontal direction;
   an illumination part for irradiating said specimen container with light; and
   an imaging part for photographing said specimen container illuminated by said illumination part,
   said holding mechanism including
      a rotating plate extending horizontally in plate-like form, and
      a main body portion for pivoting said rotating plate forwardly in a circumferential direction around a vertically extending central axis by means of elastic force of a spring,
   said rotating plate including
      a front wing portion extending in a radial direction from said central axis, and
      a protruding portion protruding forwardly in said circumferential direction from said front wing portion,
   wherein said specimen container is urged in a second direction as seen in top view to align along said first extension when said rotating plate is pivoted forwardly in said circumferential direction to bring said front wing portion into contact with said specimen container,
   wherein said specimen container is urged in a first direction as seen in top view to align along said second extension when said rotating plate is pivoted forwardly in said circumferential direction to bring said protruding portion into contact with said specimen container,
   wherein said rotating plate has a through hole extending through said rotating plate along said central axis,
   wherein said main body portion includes
      said spring that is a torsion spring,
      a fixed shaft passing through said through hole of said rotating plate and extending through a radially inner portion of a coil portion of said spring along said central axis, said fixed shaft being fixed to said table, and
      a restriction portion for restricting a rearward movement of a first arm portion of said spring in said circumferential direction, and
   wherein said rotating plate includes an abutment portion in contact with a forward portion of a second arm portion of said spring as seen in said circumferential direction.

2. The imaging device according to claim 1,
   wherein said specimen container is placed in a position below said second extension and to the right of said first extension as seen in top view,
   wherein said specimen container is urged leftwardly as seen in top view to align along said first extension when said rotating plate is pivoted forwardly in said circumferential direction to bring said front wing portion into contact with said specimen container, and
   wherein said specimen container is urged upwardly as seen in top view to align along said second extension when said rotating plate is pivoted forwardly in said circumferential direction to bring said protruding portion into contact with said specimen container.

3. An imaging device for acquiring an image of a plate-like specimen container having a rectangular shape as seen in top view, comprising:
   a table for placing said specimen container thereon;
   a position reference member provided on an upper surface of said table and including a first extension and a second extension, said first and second extensions extending in directions intersecting at right angles to each other as seen in top view;
   a holding mechanism provided on the upper surface of said table and for aligning said specimen container along said position reference member;
   a movement mechanism for moving said table, said position reference member, and said holding mechanism in a horizontal direction;
   an illumination part for irradiating said specimen container with light; and
   an imaging part for photographing said specimen container illuminated by said illumination part,
   said holding mechanism including
   a rotating plate extending horizontally in plate-like form, and a main body portion for pivoting said rotating plate forwardly in a circumferential direction around a vertically extending central axis by means of elastic force of a spring,
said rotating plate including
a front wing portion extending in a radial direction from said central axis, and
a protruding portion protruding forwardly in said circumferential direction from said front wing portion,
wherein said specimen container is urged in a second direction as seen in top view to align along said first extension when said rotating plate is pivoted forwardly in said circumferential direction to bring said front wing portion into contact with said specimen container,
wherein said specimen container is urged in a first direction as seen in top view to align along said second extension when said rotating plate is pivoted forwardly in said circumferential direction to bring said protruding portion into contact with said specimen container, and
wherein an angle between a first line extending along a forward edge of said front wing portion as seen in said circumferential direction and a second line connecting a forward end point of said protruding portion as seen in said circumferential direction and a point at which said first line contacts said protruding portion is not greater than 135° as seen in top view.

4. The imaging device according to claim 3,
wherein said specimen container is placed in a position below said second extension and to the right of said first extension as seen in top view,
wherein said specimen container is urged leftwardly as seen in top view to align along said first extension when said rotating plate is pivoted forwardly in said circumferential direction to bring said front wing portion into contact with said specimen container, and
wherein said specimen container is urged upwardly as seen in top view to align along said second extension when said rotating plate is pivoted forwardly in said circumferential direction to bring said protruding portion into contact with said specimen container.

5. An imaging device for acquiring an image of a plate-like specimen container having a rectangular shape as seen in top view, comprising:
a table for placing said specimen container thereon;
a position reference member provided on an upper surface of said table and including a first extension and a second extension, said first and second extensions extending in directions intersecting at right angles to each other as seen in top view;
a holding mechanism provided on the upper surface of said table and for aligning said specimen container along said position reference member;
a movement mechanism for moving said table, said position reference member, and said holding mechanism in a horizontal direction;
an illumination part for irradiating said specimen container with light; and
an imaging part for photographing said specimen container illuminated by said illumination part,
said holding mechanism including
a rotating plate extending horizontally in plate-like form, and
a main body portion for pivoting said rotating plate forwardly in a circumferential direction around a vertically extending central axis by means of elastic force of a spring,
said rotating plate including
a front wing portion extending in a radial direction from said central axis, and
a protruding portion protruding forwardly in said circumferential direction from said front wing portion,
wherein said specimen container is urged in a second direction as seen in top view to align along said first extension when said rotating plate is pivoted forwardly in said circumferential direction to bring said front wing portion into contact with said specimen container,
wherein said specimen container is urged in a first direction as seen in top view to align along said second extension when said rotating plate is pivoted forwardly in said circumferential direction to bring said protruding portion into contact with said specimen container, and
wherein said protruding portion protrudes in a semicircular shape forwardly in said circumferential direction as seen in top view.

6. The imaging device according to claim 5,
wherein said specimen container is placed in a position below said second extension and to the right of said first extension as seen in top view,
wherein said specimen container is urged leftwardly as seen in top view to align along said first extension when said rotating plate is pivoted forwardly in said circumferential direction to bring said front wing portion into contact with said specimen container, and
wherein said specimen container is urged upwardly as seen in top view to align along said second extension when said rotating plate is pivoted forwardly in said circumferential direction to bring said protruding portion into contact with said specimen container.

7. An imaging device for acquiring an image of a plate-like specimen container having a rectangular shape as seen in top view, comprising:
a table for placing said specimen container thereon;
a position reference member provided on an upper surface of said table and including a first extension and a second extension, said first and second extensions extending in directions intersecting at right angles to each other as seen in top view;
a holding mechanism provided on the upper surface of said table and for aligning said specimen container along said position reference member;
a movement mechanism for moving said table, said position reference member, and said holding mechanism in a horizontal direction;
an illumination part for irradiating said specimen container with light; and
an imaging part for photographing said specimen container illuminated by said illumination part,
said holding mechanism including
a rotating plate extending horizontally in plate-like form, and
a main body portion for pivoting said rotating plate forwardly in a circumferential direction around a vertically extending central axis by means of elastic force of a spring,
said rotating plate including
a front wing portion extending in a radial direction from said central axis, and
a protruding portion protruding forwardly in said circumferential direction from said front wing portion,
wherein said specimen container is urged in a second direction as seen in top view to align along said first extension when said rotating plate is pivoted forwardly in said circumferential direction to bring said front wing portion into contact with said specimen container, wherein said specimen container is urged in a first direction as seen in top view to align along said second extension when said rotating plate is pivoted forwardly in said circumferential direction to bring said protruding portion into contact with said specimen container, wherein said rotating plate further includes a rear wing portion extending in a radial direction from said central axis and positioned rearward from said front wing portion in said circumferential direction, and wherein said movement mechanism reciprocally moves said table, said position reference member, and said holding mechanism in a horizontal direction between an imaging position and a retracted position spaced apart from said imaging position, said imaging device further comprising a stopper member coming in contact with said rear wing portion to pivot said rotating plate rearwardly in said circumferential direction around said central axis to thereby release an urging force exerted on said specimen container, when said table, said position reference member, and said holding mechanism move to said retracted position.

8. The imaging device according to claim 7, wherein said specimen container is placed in a position below said second extension and to the right of said first extension as seen in top view, wherein said specimen container is urged leftwardly as seen in top view to align along said first extension when said rotating plate is pivoted forwardly in said circumferential direction to bring said front wing portion into contact with said specimen container, and wherein said specimen container is urged upwardly as seen in top view to align along said second extension when said rotating plate is pivoted forwardly in said circumferential direction to bring said protruding portion into contact with said specimen container.

* * * * *